(12) United States Patent
Snyder et al.

(10) Patent No.: US 10,363,211 B2
(45) Date of Patent: *Jul. 30, 2019

(54) HAIR CONDITIONING COMPOSITIONS COMPRISING LOW VISCOSITY EMULSIFIED SILICONE POLYMERS

(71) Applicant: The Procter & Gamble Company, Cincinnati, OH (US)

(72) Inventors: Michael Albert Snyder, Mason, OH (US); Martha Jane Weaver, Pleasant Plain, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/498,215

(22) Filed: Sep. 26, 2014

(65) Prior Publication Data

US 2015/0093420 A1 Apr. 2, 2015

Related U.S. Application Data

(60) Provisional application No. 61/883,680, filed on Sep. 27, 2013.

(51) Int. Cl.

| | |
|---|---|
| *A61K 8/00* | (2006.01) |
| *A61K 8/89* | (2006.01) |
| *A61Q 5/12* | (2006.01) |
| *A61K 8/04* | (2006.01) |
| *A61K 8/34* | (2006.01) |
| *A61K 8/41* | (2006.01) |
| *A61K 8/898* | (2006.01) |

(52) U.S. Cl.
CPC ............... *A61K 8/89* (2013.01); *A61K 8/042* (2013.01); *A61K 8/34* (2013.01); *A61K 8/416* (2013.01); *A61K 8/898* (2013.01); *A61Q 5/12* (2013.01); *A61K 2800/412* (2013.01); *A61K 2800/5426* (2013.01)

(58) Field of Classification Search
CPC ...... A61K 2800/412; A61K 2800/5426; A61K 8/042; A61K 8/34; A61K 8/416; A61K 8/89; A61K 8/898; A61Q 5/12
See application file for complete search history.

(56) References Cited

U.S. PATENT DOCUMENTS

| | | | |
|---|---|---|---|
| 4,529,586 A | 7/1985 | De Marco et al. | |
| 4,533,714 A | 8/1985 | Sebag et al. | |
| 4,587,321 A | 5/1986 | Sebag et al. | |
| 4,597,962 A | 7/1986 | Grollier et al. | |
| 4,673,568 A | 6/1987 | Grollier et al. | |
| 4,833,225 A | 5/1989 | Schaefer et al. | |
| 4,891,166 A | 1/1990 | Schaefer et al. | |
| 4,902,499 A | 2/1990 | Bolish, Jr. et al. | |
| 4,921,895 A | 5/1990 | Schaefer et al. | |
| 5,098,979 A | 3/1992 | O'Lenick, Jr. | |
| 5,100,658 A | 3/1992 | Bolich, Jr. et al. | |
| 5,153,294 A * | 10/1992 | O'Lenick, Jr. ................. 528/26 |
| 5,166,297 A | 11/1992 | O'Lenick, Jr. | |
| 5,196,499 A | 3/1993 | Olenick, Jr. | |
| 5,714,446 A | 2/1998 | Bartz | |
| 5,760,136 A * | 6/1998 | Kato et al. ................. 525/100 |
| 5,932,203 A * | 8/1999 | Coffindaffer et al. ...... 424/70.19 |
| 5,998,537 A | 12/1999 | Good et al. | |
| 6,013,682 A | 1/2000 | Dalle et al. | |
| 6,136,304 A | 10/2000 | Pyles | |
| 6,193,961 B1 * | 2/2001 | Liu et al. ................. 424/70.12 |
| 6,207,141 B1 | 3/2001 | Pyles | |
| 6,240,929 B1 | 6/2001 | Richard et al. | |
| 6,242,554 B1 | 6/2001 | Busch et al. | |
| 6,475,568 B1 | 11/2002 | Czech | |
| 6,482,399 B2 | 11/2002 | Pyles | |
| 6,482,969 B1 | 11/2002 | Helmrick et al. | |
| 6,589,519 B1 | 7/2003 | Restle et al. | |
| 6,607,717 B1 | 8/2003 | Johnson et al. | |
| 6,640,280 B1 | 10/2003 | Kamvysselis et al. | |
| 6,649,689 B2 | 11/2003 | Gosselink et al. | |
| 6,696,052 B2 | 2/2004 | Aeby et al. | |
| 6,696,053 B1 | 2/2004 | Ma et al. | |
| 6,730,766 B2 | 5/2004 | Schattenmann et al. | |
| 6,903,061 B2 | 6/2005 | Masschelein et al. | |

(Continued)

FOREIGN PATENT DOCUMENTS

| | | |
|---|---|---|
| EP | 0490582 A1 | 6/1992 |
| EP | 0 532 272 A | 3/1993 |

(Continued)

OTHER PUBLICATIONS

U.S. Appl. No. 14/498,246, filed Sep. 26, 2014, Snyder.
U.S. Appl. No. 14/923,991, filed Oct. 27, 2015, Snyder et al.
PCT International Search Report and Written Opinion for PCT/US2014/055777 dated Jan. 29, 2015, 12 pages.
PCT International Search Report and Written Opinion for PCT/US2014/055778 dated Jan. 29, 2015, 16 pages.

(Continued)

*Primary Examiner* — Robert A Wax
*Assistant Examiner* — Olga V Tcherkasskaya
(74) *Attorney, Agent, or Firm* — Angela K. Haughey

(57) ABSTRACT

Embodiments of a hair conditioning composition include a silicone polymer comprising one or more quaternary groups, at least one silicone block comprising greater than 200 siloxane units, at least one polyalkylene oxide structural unit, and at least one terminal ester group. The silicone polymer has a viscosity of up to 100,000 mPa·s. The silicone polymer is added to create a pre-emulsified dispersion with a particle size of less than about 1 micron. The hair conditioning composition includes a gel matrix including a cationic surfactant, a high melting point fatty compound, and an aqueous carrier.

9 Claims, No Drawings

(56) References Cited

U.S. PATENT DOCUMENTS

| | | | |
|---|---|---|---|
| 7,041,767 | B2 | 5/2006 | Lange et al. |
| 7,087,650 | B2 | 8/2006 | Lennon |
| 7,186,406 | B2 | 3/2007 | Decoster et al. |
| 7,217,777 | B2 | 5/2007 | Lange et al. |
| 7,223,384 | B1 | 5/2007 | Decoster et al. |
| 7,235,749 | B2 | 6/2007 | Imoto |
| 7,384,903 | B2 | 6/2008 | Masschelein et al. |
| 7,390,479 | B2 | 6/2008 | Sockel et al. |
| 7,563,856 | B2 | 7/2009 | Lange et al. |
| 7,563,857 | B2 | 7/2009 | Lange et al. |
| 7,585,494 | B2 | 9/2009 | Lange et al. |
| 7,740,873 | B2 | 6/2010 | Decoster et al. |
| 7,863,397 | B2 | 1/2011 | Lange et al. |
| 8,076,442 | B2 * | 12/2011 | Moeller et al. ............... 528/28 |
| 8,362,185 | B2 * | 1/2013 | Wagner et al. ............... 528/20 |
| 9,198,849 | B2 | 12/2015 | Snyder et al. |
| 2003/0143177 | A1 | 7/2003 | Stella |
| 2004/0120914 | A1 | 6/2004 | Decoster et al. |
| 2004/0126349 | A1 | 7/2004 | Anderson et al. |
| 2004/0265258 | A1 | 12/2004 | Robinson et al. |
| 2005/0002871 | A1 | 1/2005 | Ivanova et al. |
| 2005/0048016 | A1 | 3/2005 | Lebreton et al. |
| 2005/0169878 | A1 | 8/2005 | Elder et al. |
| 2006/0154848 | A1 | 7/2006 | Girboux et al. |
| 2006/0233720 | A1 | 10/2006 | Stork et al. |
| 2007/0041929 | A1 * | 2/2007 | Torgerson et al. ...... 424/70.122 |
| 2007/0286837 | A1 | 12/2007 | Torgerson et al. |
| 2008/0029575 | A1 | 2/2008 | Shelton et al. |
| 2008/0292575 | A1 | 11/2008 | Uehara |
| 2009/0142293 | A1 * | 6/2009 | Wagner et al. ............ 424/78.37 |
| 2011/0126849 | A1 | 6/2011 | Isaacs |
| 2011/0135588 | A1 | 6/2011 | Uehara et al. |
| 2012/0052038 | A1 | 3/2012 | Panandiker et al. |
| 2013/0259817 | A1 * | 10/2013 | Uehara et al. ............ 424/70.11 |
| 2013/0259820 | A1 * | 10/2013 | Snyder et al. ........... 424/70.122 |
| 2013/0280193 | A1 * | 10/2013 | Carter et al. .................... 424/62 |
| 2014/0302103 | A1 * | 10/2014 | Carter et al. .................. 424/401 |
| 2015/0010487 | A1 | 1/2015 | Snyder et al. |
| 2015/0011449 | A1 | 1/2015 | Snyder |
| 2015/0037273 | A1 | 2/2015 | Wagner |
| 2015/0056155 | A1 | 2/2015 | Wagner |
| 2015/0093420 | A1 | 4/2015 | Snyder et al. |
| 2015/0093421 | A1 | 4/2015 | Snyder et al. |

FOREIGN PATENT DOCUMENTS

| | | |
|---|---|---|
| EP | 1108416 B1 | 6/2006 |
| EP | 1093808 B1 | 7/2006 |
| EP | 1093809 B1 | 10/2006 |
| EP | 1093807 B1 | 4/2007 |
| EP | 1093805 B1 | 2/2008 |
| GB | 2161172 A | 1/1986 |
| JP | 5818812 A | 11/1983 |
| WO | 1999/32539 A1 | 7/1999 |
| WO | 2000/07551 A1 | 2/2000 |
| WO | 2001/41719 A1 | 6/2001 |
| WO | 2001/41720 A1 | 6/2001 |
| WO | 2001/41721 A1 | 6/2001 |
| WO | 2002/062311 A1 | 8/2002 |
| WO | 2004/039338 A1 | 5/2004 |
| WO | 2004/047779 A2 | 6/2004 |
| WO | 2004/069137 A1 | 8/2004 |
| WO | 2013/148935 A1 | 10/2013 |

OTHER PUBLICATIONS

All Office Actions, U.S. Appl. No. 14/923,991, P&G Case 12989MC.
All Office Actions, U.S. Appl. No. 14/039,929, P&G Case 12990M.
All Office Actions, U.S. Appl. No. 14/498,246, P&G Case 13084M.
PCT International Search Report and Written Opinion for PCT/US2014/044329 dated Oct. 27, 2014.

* cited by examiner

HAIR CONDITIONING COMPOSITIONS COMPRISING LOW VISCOSITY EMULSIFIED SILICONE POLYMERS

TECHNICAL FIELD OF THE INVENTION

Provided is a hair conditioning composition comprising silicone polymers and a gel matrix. The silicone polymers have lower viscosities, for example, up to 100,000 mPa·s, which allow the composition to provide improved conditioning benefits such as smooth feel and reduced friction to both damaged hair and non-damaged hair without the need for a silicone blend. The silicone polymers may be added to create a pre-emulsified dispersion with a particle size of less than about 1 micron.

BACKGROUND OF THE INVENTION

Silicone polymers are strategically important materials in hair care, especially in providing conditioning benefits to hair. Human hair becomes damaged due to, for example, shampooing, combing, permanent waves, and/or coloring the hair. Such damaged hair is often left hydrophilic and/or in a rough condition especially when the hair dries, compared to non-damaged or less damaged hair. Silicone polymers consisting of blocks of silicones and alkylene oxide (e.g., ethylene oxide and propylene oxide groups (EO/PO)) linked with amine- and quat-functional groups have been used to counteract the hydrophilic nature of damaged hair. Silicone blocks are responsible for conditioning and lubrication performance while amine- and quat-functional groups included in the polymer chain further aid deposition during rinsing. In particular, optimum conditioning performance has been observed for silicone blocks of greater than 200 D units. D units represents the dimethylsiloxane units in a linear silicone polymer. However these materials generally have high viscosities as neat materials. In order to achieve the desired conditioning benefits, these silicone polymers have traditionally been used in blends with silicone copolyols or other diluents or solvents.

Based on the foregoing, there is a need for hair conditioning compositions which provide even greater improved conditioning benefits such as smooth feel and reduced friction on wet hair and dry hair. In addition, there is a need for hair conditioning compositions which provide improved conditioning benefits on damaged hair.

There is also a need for a composition that minimizes the need for additional blend materials in combination with silicone polymers, while delivering the above mentioned combination of benefits with lower cost and complexity than the traditional blend materials.

SUMMARY OF THE INVENTION

Without being bound by theory, the low viscosity silicone polymers in the hair conditioning compositions described herein provide improved conditioning benefits to both damaged hair and non-damaged hair while eliminating the need for a silicone blend. These benefits are enhanced when the silicone polymers are a pre-emulsified dispersion with a particle size of less than about 1 micron. In an embodiment, the pre-emulsified low viscosity silicone polymers in the hair conditioning compositions described herein provide improved conditioning with the use of less silicone polymers.

In accordance with one embodiment, the hair conditioning compositions may comprise a silicone polymer comprising one or more quaternary groups, at least one silicone block comprising greater than 200 siloxane units, at least one polyalkylene oxide structural unit, and at least one terminal ester group, wherein the silicone polymer has a viscosity of up to 100,000 mPa·s, wherein said silicone polymer is added to create a pre-emulsified dispersion with a particle size of less than about 1 micron, and wherein the a hair conditioning composition comprises a gel matrix comprising a cationic surfactant, a high melting point fatty compound, and an aqueous carrier.

These and additional features provided by the embodiments of the present invention will be more fully understood in view of the following detailed description.

DETAILED DESCRIPTION OF THE INVENTION

Components of the personal care compositions (e.g., hair conditioning composition) are described below. Also included is a nonexclusive description of various optional and preferred components useful in embodiments of the personal care composition described herein. While the specification concludes with claims that particularly point out and distinctly claim the invention, it is believed the personal care composition described herein will be better understood from the following description.

All percentages, parts, and ratios are based upon the total weight of the compositions described herein, unless otherwise specified. All such weights as they pertain to listed ingredients are based on the active level and, therefore, do not include solvents or by-products that may be included in commercially available materials, unless otherwise specified. The term "weight percent" may be denoted as "wt. %" herein.

All molecular weights as used herein are weight average molecular weights expressed as grams/mole, unless otherwise specified.

The compositions and methods/processes of the personal care composition described herein can comprise, consist of, and consist essentially of the essential elements and limitations of the invention described herein, as well as any of the additional or optional ingredients, components, steps, or limitations described herein.

Herein, "mixtures" is meant to include a simple combination of materials and any compounds that may result from their combination.

As used herein, "indicia" means an identifying mark, including text and/or graphics.

As used herein, "image" means a photograph, illustration, and/or other pictorial representation of an object.

Embodiments of the hair conditioning composition described herein comprise silicone polymers having a viscosity of up to 100,000 mPa·s. These compositions are prepared by a method comprising the step of mixing the silicone polymer containing quaternary groups with the gel matrix.

Damaged hair is less hydrophobic compared to non-damaged and/or less damaged hair. It is believed that by providing improved hydrophobicity to hair, the hair conditioning composition can provide improved smooth feel and reduced friction to the hair. It is also believed that the improved hydrophobicity to the hair can be provided by some other preferred features of the personal care composition described herein, for example, the use of additional materials such as silicones, and/or cationic surfactants. Further, without being limited to the theory, it is believed that improved hydrophobicity provides improved tolerance to the hair for humidity in the surrounding circumstances, and thus provides reduced frizziness and/or fly-aways on rainy and/or humid days.

The hair conditioning composition described herein has a pH of from about 2 to about 9, alternatively from about 3 to about 7.

A. Silicone Polymer Containing Quaternary Groups

The personal care composition described herein may comprise a low viscosity silicone polymer having a viscosity up to 100,000 mPa·s. Without being bound by theory, this low viscosity silicone polymer provides improved conditioning benefits such as smooth feel, reduced friction, and prevention of hair damage, while eliminating the need for a silicone blend.

Structurally, the silicone polymer is a polyorganosiloxane compound comprising one or more quaternary ammonium groups, at least one silicone block comprising greater than 200 siloxane units, at least one polyalkylene oxide structural unit, and at least one terminal ester group. In one or more embodiments, the silicone block may comprise between 300 to 500 siloxane units.

The silicone polymer is present in an amount of from about 0.05% to about 15%, alternatively from about 0.1% to about 10%, alternatively from about 0.15% to about 5%, and alternatively from about 0.2% to about 4% by weight of the composition.

In a preferred embodiment the polyorganosiloxane compounds according to the invention have the general formulas (Ia) and (Ib):

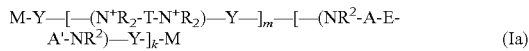
(Ia)

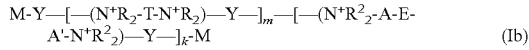
(Ib)

wherein:
m is >0, preferred 0.01 to 100, more preferred 0.1 to 100, even more preferred 1 to 100, specifically 1 to 50, more specifically 1 to 20, even more specifically 1 to 10, wherein m is a weight-average degree of polymerization;
k is 0 or an average value of from >0 to 50, or alternatively from 1 to 20, or alternatively from 1 to 10, wherein k is a weight-average degree of polymerization;
M represents a terminal group, comprising terminal ester groups selected from
—OC(O)—Z
—OS(O)$_2$—Z
—OS(O$_2$)O—Z
—OP(O)(O—Z)OH
—OP(O)(O—Z)$_2$
wherein Z is selected from monovalent organic residues having up to 40 carbon atoms, optionally comprising one or more hetero atoms.

A and A' each are independently from each other selected from a divalent organic group having up to 10 carbon atoms and one or more hetero atoms, and
E is a polyalkylene oxide group of the general formula:

wherein q=0 to 200, r=0 to 200, s=0 to 200, and q+r+s=1 to 600.
R$^2$ is selected from hydrogen or R,
R is selected from monovalent organic groups having up to 22 carbon atoms and optionally one or more heteroatoms, and wherein the free valencies at the nitrogen atoms are bound to carbon atoms, Y is a group of the formula:

—K—S—K— and -A-E-A'- or -A'-E-A-,

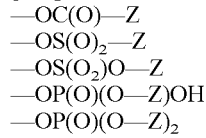

with S=
wherein R$^1$=C$_1$-C$_{22}$-alkyl, C$_1$-C$_{22}$-fluoralkyl or aryl; n=200 to 1000, and these can be identical or different if several S groups are present in the polyorganosiloxane compound.

K is a bivalent or trivalent straight chain, cyclic and/or branched C$_2$-C$_{40}$ hydrocarbon residue which is optionally interrupted by —O—, —NH—, trivalent N, —NR$^1$—, —C(O)—, —C(S)—, and optionally substituted with —OH, wherein R$^1$ is defined as above, T is selected from a divalent organic group having up to 20 carbon atoms and one or more hetero atoms.

The residues K may be identical or different from each other. In the —K—S—K— moiety, the residue K is bound to the silicon atom of the residue S via a C—Si-bond.

Due to the possible presence of amine groups (—(NR$^2$-A-E-A'-NR$^2$)—) in the polyorganosiloxane compounds, they may have protonated ammonium groups, resulting from the protonation of such amine groups with organic or inorganic acids. Such compounds are sometimes referred to as acid addition salts of the polyorganosiloxane compounds according to the invention.

In a preferred embodiment the molar ratio of the quaternary ammonium groups b) and the terminal ester groups c) is less than 100:20, even more preferred is less than 100:30 and is most preferred less than 100:50. The ratio can be determined by $^{13}$C-NMR.

In a further embodiment, the polyorganosiloxane composition may comprise:
A) at least one polyorganosiloxane compound, comprising a) at least one polyorganosiloxane group, b) at least one quaternary ammonium group, c) at least one terminal ester group, and d) at least one polyalkylene oxide group (as defined before),
B) at least one polyorganosiloxane compound, comprising at least one terminal ester group, different from compound A).

In the definition of component A) it can be referred to the description of the polyorganosiloxane compounds of the invention. The polyorganosiloxane compound B) differs from the polyorganosiloxane compound A) alternatively in that it does not comprise quaternary ammonium groups. Preferred polyorganosiloxane compounds B) result from the reaction of monofunctional organic acids, in particular carboxylic acids, and polyorganosiloxane containing bisepoxides.

In the polyorganosiloxane compositions according to the invention the weight ratio of compound A) to compound B) is alternatively less than 90:10. Or in other words, the content of component B) is at least 10 weight percent. In a further preferred embodiment of the polyorganosiloxane compositions according to the invention in compound A) the molar ratio of the quaternary ammonium groups b) and the terminal ester groups c) is less than 100:10, even more preferred is less than 100:15 and is most preferred less than 100:20.

The silicone polymer has a viscosity at 20° C. at 100% concentration silicone polymer with no additional solvents and a shear rate of 0.1 s$^{-1}$ (plate-plate system, plate diameter 40 mm, gap width 0.5 mm) of less than 100,000 mPa·s (100 Pa·s). In further embodiments, the viscosities of the neat silicone polymers may range from 500 to 100,000 mPa·s, or alternatively from 500 to 70,000 mPa·s, or alternatively from 500 to 50,000 mPa·s, or alternatively from 500 to 20,000 mPa·s. In further embodiments, the viscosities of the neat polymers may range from 500 to 10,000 mPa·s, or alternatively 500 to 5000 mPa·s determined at 20° C. at 100% concentration silicone polymer with no additional solvents and a shear rate of 0.1 s$^{-1}$.

In addition to the above listed silicone polymers, the following preferred compositions are provided below. For example, in the polyalkylene oxide group E of the general formula:

—[CH$_2$CH$_2$O]$_q$—[CH$_2$CH(CH$_3$)O]$_r$—[CH$_2$CH(C$_2$H$_5$)O]$_s$— wherein the q, r, and s indices may be defined as follows:
q=0 to 200, or alternatively from 0 to 100, or alternatively from 0 to 50, or alternatively from 0 to 20,
r=-0 to 200, or alternatively from 0 to 100, or alternatively from 0 to 50, or alternatively from 0 to 20,
s=0 to 200, or alternatively from 0 to 100, or alternatively from 0 to 50, or alternatively from 0 to 20,
and q+r+s=1 to 600, or alternatively from 1 to 100, or alternatively from 1 to 50, or alternatively from 1 to 40.

For polyorganosiloxane structural units with the general formula S:

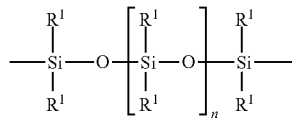

R$^1$=C$_1$-C$_{22}$-alkyl, C$_1$-C$_{22}$-fluoralkyl or aryl; n=from 200 to 1000, or alternatively from 300 to 500, K (in the group —K—S—K—) is alternatively a bivalent or trivalent straight chain, cyclical or branched C$_2$-C$_{20}$ hydrocarbon residue which is optionally interrupted by —O—, —NH—, trivalent N, —NR$^1$—, —C(O)—, —C(S)—, and optionally substituted with —OH.

In specific embodiments, R$^1$ is C$_1$-C$_{18}$ alkyl, C$_1$-C$_{18}$ fluoroalkyl and aryl. Furthermore, R$^1$ is alternatively C$_1$-C$_{18}$ alkyl, C$_1$-C$_6$ fluoroalkyl and aryl. Furthermore, R$^1$ is alternatively C$_1$-C$_6$ alkyl, C$_1$-C$_6$ fluoroalkyl, alternatively C$_1$-C$_4$ fluoroalkyl, and phenyl. Most alternatively, R$^1$ is methyl, ethyl, trifluoropropyl and phenyl.

As used herein, the term "C$_1$-C$_{22}$ alkyl" means that the aliphatic hydrocarbon groups possess from 1 to 22 carbon atoms which can be straight chain or branched. Methyl, ethyl, propyl, n-butyl, pentyl, hexyl, heptyl, nonyl, decyl, undecyl, isopropyl, neopentyl and 1,2,3-trimethyl hexyl moieties serve as examples.

Further as used herein, the term "C$_1$-C$_{22}$ fluoroalkyl" means aliphatic hydrocarbon compounds with 1 to 22 carbon atoms which can be straight chain or branched and are substituted with at least one fluorine atom. Monofluormethyl, monofluoroethyl, 1,1,1-trifluorethyl, perfluoroethyl, 1,1,1-trifluoropropyl, 1,2,2-trifluorobutyl are suitable examples.

Moreover, the term "aryl" means unsubstituted or phenyl substituted once or several times with OH, F, Cl, CF$_3$, C$_1$-C$_6$ alkyl, C$_1$-C$_6$ alkoxy, C$_3$-C$_7$ cycloalkyl, C$_2$-C$_6$ alkenyl or phenyl. Aryl may also mean naphthyl.

For the embodiments of the polyorganosiloxanes, the positive charges resulting from the ammonium group(s), are neutralized with inorganic anions such as chloride, bromide, hydrogen sulfate, sulfate, or organic anions, like carboxylates deriving from C$_1$-C$_{30}$ carboxylic acids, for example acetate, propionate, octanoate, especially from C$_{10}$-C$_{18}$ carboxylic acids, for example decanoate, dodecanoate, tetradecanoate, hexadecanoate, octadecanoate and oleate, alkylpolyethercarboxylate, alkylsulphonate, arylsulphonate, alkylarylsulphonate, alkylsulphate, alkylpolyethersulphate, phosphates derived from phosphoric acid mono alkyl/aryl ester and phosphoric acid dialkyl/aryl ester. The properties of the polyorganosiloxane compounds can be, inter alia, modified based upon the selection of acids used.

The quaternary ammonium groups are usually generated by reacting the di-tertiary amines with an alkylating agents, selected from in particular di-epoxides (sometimes referred to also as bis-epoxides) in the presence of mono carboxylic acids and difunctional dihalogen alkyl compounds.

In a preferred embodiment the polyorganosiloxane compounds are of the general formulas (Ia) and (Ib):

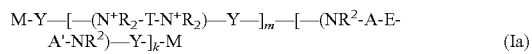
M-Y—[—(N$^+$R$_2$-T-N$^+$R$_2$)—Y—]$_m$—[—(NR$^2$-A-E-A'-NR$^2$)—Y-]$_k$-M (Ia)

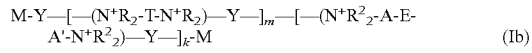
M-Y—[—(N$^+$R$_2$-T-N$^+$R$_2$)—Y—]$_m$—[—(N$^+$R$^2$$_2$-A-E-A'-N$^+$R$^2$$_2$)—Y—]$_k$-M (Ib)

wherein each group is as defined above; however, the repeating units are in a statistical arrangement (i.e., not a block-wise arrangement).

In a further preferred embodiment the polyorganosiloxane compounds may be also of the general formulas (IIa) or (IIb):

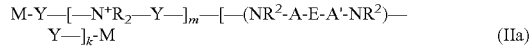
M-Y—[—N$^+$R$_2$—Y—]$_m$—[—(NR$^2$-A-E-A'-NR$^2$)—Y—]$_k$-M (IIa)

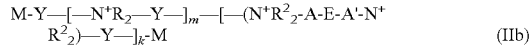
M-Y—[—N$^+$R$_2$—Y—]$_m$—[—(N$^+$R$^2$$_2$-A-E-A'-N$^+$R$^2$$_2$)—Y—]$_k$-M (IIb)

wherein each group is as defined above. Also in such formula the repeating units are usually in a statistical arrangement (i.e not a block-wise arrangement).

wherein, as defined above, M is
—OC(O)—Z,
—OS(O)$_2$—Z
—OS(O$_2$)O—Z
—OP(O)(O—Z)OH
—OP(O)(O—Z)$_2$

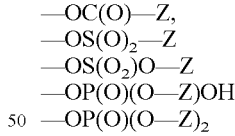

Z is a straight chain, cyclic or branched saturated or unsaturated C$_1$-C$_{20}$, or alternatively C$_2$ to C$_{18}$, or alternatively a hydrocarbon radical, which can be interrupted by one or more —O—, or —C(O)— and substituted with —OH. In a specific embodiment, M is —OC(O)—Z resulting from normal carboxylic acids in particular with more than 10 carbon atoms like for example dodecanoic acid.

In a further embodiment, the molar ratio of the polyorganosiloxane-containing repeating group —K—S—K— and the polyalkylene repeating group -A-E-A'- or -A'-E-A- is between 100:1 and 1:100, or alternatively between 20:1 and 1:20, or alternatively between 10:1 and 1:10.

In the group —(N$^+$R$_2$-T-N$^+$R$_2$)—, R may represent a monovalent straight chain, cyclic or branched C$_1$-C$_{20}$ hydrocarbon radical, which can be interrupted by one or more —O—, —C(O)— and can be substituted by —OH, T may represent a divalent straight-chain, cyclic, or branched $C_1$-$C_{20}$ hydrocarbon radical, which can be interrupted by —O—, —C(O)— and can be substituted by hydroxyl.

The above described polyorganosiloxane compounds comprising quaternary ammonium functions and ester functions may also contain: 1) individual molecules which contain quaternary ammonium functions and no ester functions; 2) molecules which contain quaternary ammonium functions and ester functions; and 3) molecules which contain ester functions and no quaternary ammonium functions. While not limited to structure, the above described polyorganosiloxane compounds comprising quaternary ammonium functions and ester functions are to be understood as mixtures of molecules comprising a certain averaged amount and ratio of both moieties.

Various monofunctional organic acids may be utilized to yield the esters. Exemplary embodiments include $C_1$-$C_{30}$ carboxylic acids, for example $C_2$, $C_3$, $C_8$ acids, $C_{10}$-$C_{18}$ carboxylic acids, for example $C_{12}$, $C_{14}$, $C_{16}$ acids, saturated, unsaturated and hydroxyl functionalized $C_{18}$ acids, alkylpolyethercarboxylic acids, alkylsulphonic acids, arylsulphonic acids, alkylarylsulphonic acids, alkylsulphuric acids, alkylpolyethersulphuric acids, phosphoric acid mono alkyl/aryl esters and phosphoric acid dialkyl/aryl esters.

Further performance improvements can be achieved by pre-dispersing the silicone polymer in a small particle emulsion (less than 1 micron) prior to adding it to the conditioner base.

The term "emulsion" in this patent application describes any stable emulsion or dispersion of the silicone polymer, separately prepared and used as one of the components of a conditioner composition.

Stable means that the viscosity, particle size, and other important characteristics of the emulsion do not significantly change over reasonable time under exposure to typical temperature, moisture, pressure, shear, light and other environmental conditions that the pre-emulsion is exposed during packing, storage, and transportation Making the small particle emulsion may require pre-emulsifying the silicone polymer before their addition to the conditioning composition. A non-limiting example of a method of making is provided below. All oil soluble components are mixed in a vessel. Heat may be applied to allow mixture to liquidify. All water soluble components are mixed in a separate vessel and heated to about same temperature as the oil phase. The oil phase and aqueous phase are mixed under a high shear mixer (example, Turrax mixer by IKA). The particle size of the silicone polymer is in the range of about 0.01 μm to about 5 μm, alternatively from 0.05 μm to about 1 μm, alternatively from about 0.1 μm to about 0.5 μm. High energy mixing device may be used to achieve desired particle size. High energy mixing device include, but not limited to Microfluidizer from Microfluidics Corp., Sonolator from Sonic Corp., Colloid mill from Sonic Corp.

The emulsifiers which may be selected for each the silicone may be guided by the Hydrophilic-Lipophilic-Balance value (HLB value) of emulsifiers. Suitable range of HLB value may be 6-16, alternatively 8-14. Emulsifiers with a HLB higher than 10 are water soluble. Emulsifiers with low HLB are lipid soluble. To obtain suitable HLB value, a mixture of two or more emulsifiers may be used. Suitable emulsifiers include non-ionic, cationic, anionic and amphoteric emulsifiers.

The concentration of the emulsifier in the emulsion and the emulsifications of the silicone polymer should be sufficient to achieve desired particle size and emulsion stability, and generally ranges from about 0.1 wt %-about 50 wt %, from about 1 wt %-about 30 wt %, from about 2 wt %-about 20 wt %, for example.

The use of a pre-emulsified dispersion of the silicone may present multiple advantages including: (i) The small particle size of the silicones in the emulsion leads to more even deposition and reduces island-like spotty deposits; and (ii) the more even deposition is more favorable for providing smoothness for hair/skin surfaces, easier combing, and enhanced hair volume.

B. Gel Matrix

The personal care composition described herein may comprise a gel matrix comprising a cationic surfactant, a high melting point fatty compound, and an aqueous carrier. The cationic surfactant, together with the high melting point fatty compound, and an aqueous carrier, provides a gel matrix which is suitable for providing various conditioning benefits, especially slippery and slick feel on wet hair. Thus, the silicone polymers containing quaternary groups (described above) and the gel matrix both provide conditioning benefits, such that when combined can impart increased functionality as compared to the individual components.

In view of providing the above gel matrix, the cationic surfactant and the high melting point fatty compound are contained at a level such that the mole ratio of the cationic surfactant to the high melting point fatty compound is in the range of, alternatively from about 1:1 to about 1:10, alternatively from about 1:2 to about 1:6 or from about 1:1 to about 1:4, in view of providing the above conditioning benefits especially slippery and slick feel on wet hair. Exemplary compositions described herein may comprise, by weight of the composition, from about 60% to about 99%, alternatively from about 70% to about 95%, and alternatively from about 80% to about 95% of a gel matrix including lamellar gel matrix, to which optional ingredients can be added (e.g., silicones).

1. Cationic Surfactant

The compositions described herein may comprise a cationic surfactant. The cationic surfactant is a mono-long alkyl quaternized ammonium salt having the formula (III):

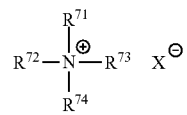

wherein one of $R^{71}$, $R^{72}$, $R^{73}$, and $R^{74}$ is selected from an aliphatic group of from about 16 to about 30 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$, $R^{73}$, and $R^{74}$ are independently selected from an aliphatic group of from about 1 to about 8 carbon atoms or an aromatic, alkoxy, polyoxyalkylene, alkylamido, hydroxyalkyl, aryl or alkylaryl group having up to about 8 carbon atoms; and $X^-$ is a salt-forming anion such as those selected from halogen, (e.g., chloride, bromide), acetate, citrate, lactate, glycolate, phosphate, nitrate, sulfonate, sulfate, alkylsulfate, glutamate, and alkyl sulfonate radicals. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Alternatively, one of $R^{71}$, $R^{72}$, $R^{73}$, and $R^{74}$ is selected from an alkyl group of from about 16 to about 30 carbon atoms, alternatively from about 18 to about 26 carbon atoms, still alternatively from about 22 carbon atoms; the remainder of $R^{71}$, $R^{72}$, $R^{73}$, and $R^{74}$ are independently selected from the group consisting of $CH_3$, $C_2H_5$, $C_2H_4OH$, $CH_2C_6H_5$, and mixtures thereof; and (X) is selected from the group consisting of Cl, Br, $CH_3OSO_3$, and mixtures thereof. It is believed that such mono-long alkyl quaternized ammonium salts can provide improved slippery and slick feel on wet hair, compared to multi-long alkyl quaternized ammonium salts. It is also believed that mono-long alkyl quaternized ammonium salts can provide improved hydrophobicity and smooth feel on dry hair, compared to amine or amine salt cationic surfactants.

Nonlimiting examples of such mono-long alkyl quaternized ammonium salt cationic surfactants include: behenyl trimethyl ammonium chloride available, for example, with tradename Genamine KDMP from Clariant, with tradename INCROQUAT TMC-80 from Croda and ECONOL TM22 from Sanyo Kasei; stearyl trimethyl ammonium chloride available, for example, with tradename CA-2450 from Nikko Chemicals; cetyl trimethyl ammonium chloride available, for example, with tradename CA-2350 from Nikko Chemicals; behenyltrimethylammonium methyl sulfate; hydrogenated tallow alkyl trimethyl ammonium chloride; stearyl dimethyl benzyl ammonium chloride; and stearoyl amidopropyl dimethyl benzyl ammonium chloride.

Among them, more preferred cationic surfactants are those having a longer alkyl group, i.e., $C_{22}$ alkyl group. Such cationic surfactant includes, for example, behenyl trimethyl ammonium chloride and behenyltrimethylammonium methyl sulfate. It is believed that cationic surfactants having a longer alkyl group provide improved hydrophobicity on dry hair, compared to cationic surfactant having a shorter alkyl group. It is also believed that compared to cationic surfactants having a shorter alkyl group, cationic surfactants having a long alkyl group can provide improved hydrophobicity to the hair, especially to damaged hair, when combined with the polyol esters of the personal care composition described herein. Alternatively, it is believed that cationic surfactant having an adequate length of alkyl group provides improved slippery and slick feel on wet hair, compared to a cationic surfactant having too long an alkyl group. Thus, it is believed that the selection of $C_{22}$ alkyl group among long alkyl groups provides balanced benefits between improved hydrophobicity on dry hair and improved slippery and slick feel on wet hair.

The compositions described herein may comprise the cationic surfactant in amount of from about 0.1% to about 10%, alternatively from about 1% to about 8%, still alternatively from about 1.5% to about 5% by weight of the composition.

2. High Melting Point Fatty Compound

The hair conditioning composition described herein may comprise a high melting point fatty compound. The high melting point fatty compounds useful herein have a melting point of about 25° C. or higher, and are selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than about 25° C. Such compounds of low melting point are not intended to be included in this section. Nonlimiting examples of the high melting point compounds are found in *International Cosmetic Ingredient Dictionary*, Fifth Edition, 1993, and *CTFA Cosmetic Ingredient Handbook*, Second Edition, 1992.

The high melting point fatty compound can be included in the composition at a level of from about 0.1% to about 20%, alternatively from about 1% to about 10%, still alternatively from about 2% to about 8%, by weight of the composition.

The fatty alcohols useful herein are those having from about 14 to about 30 carbon atoms, alternatively from about 16 to about 22 carbon atoms. These fatty alcohols are saturated and can be straight or branched chain alcohols. Nonlimiting examples of fatty alcohols include cetyl alcohol, stearyl alcohol, behenyl alcohol, and mixtures thereof.

The fatty acids useful herein are those having from about 10 to about 30 carbon atoms, alternatively from about 12 to about 22 carbon atoms, and alternatively from about 16 to about 22 carbon atoms. These fatty acids are saturated and can be straight or branched chain acids. Also included are diacids, triacids, and other multiple acids which meet the requirements herein. Also included herein are salts of these fatty acids. Nonlimiting examples of fatty acids include lauric acid, palmitic acid, stearic acid, behenic acid, sebacic acid, and mixtures thereof.

The fatty alcohol derivatives and fatty acid derivatives useful herein include alkyl ethers of fatty alcohols, alkoxylated fatty alcohols, alkyl ethers of alkoxylated fatty alcohols, esters of fatty alcohols, fatty acid esters of compounds having esterifiable hydroxy groups, hydroxy-substituted fatty acids, and mixtures thereof. Nonlimiting examples of fatty alcohol derivatives and fatty acid derivatives include materials such as methyl stearyl ether; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through steareth-10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e., a mixture of fatty alcohols containing predominantly cetyl and stearyl alcohol, wherein the numeric designation indicates the number of ethylene glycol moieties present; $C_1$-$C_{30}$ alkyl ethers of the ceteth, steareth, and ceteareth compounds just described; polyoxyethylene ethers of behenyl alcohol; ethyl stearate, cetyl stearate, cetyl palmitate, stearyl stearate, myristyl myristate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, glyceryl monostearate, glyceryl distearate, glyceryl tristearate, and mixtures thereof.

High melting point fatty compounds of a single compound of high purity are preferred. Single compounds of pure fatty alcohols selected from the group of pure cetyl alcohol, stearyl alcohol, and behenyl alcohol are highly preferred. By "pure" herein, what is meant is that the compound has a purity of at least about 90%, alternatively at least about 95%. These single compounds of high purity provide good rinsability from the hair when the consumer rinses off the composition.

Commercially available high melting point fatty compounds useful herein include: cetyl alcohol, stearyl alcohol, and behenyl alcohol available from Shin Nihon Rika (Osaka, Japan) from NOF (Tokyo, Japan); pure behenyl alcohol having tradename 1-DOCOSANOL available from WAKO (Osaka, Japan).

3. Aqueous Carrier

The hair conditioning composition described herein comprises an aqueous carrier. The level and species of the carrier are selected according to the compatibility with other components, and other desired characteristics of the product.

The carrier useful in the personal care composition described herein includes water and water solutions of lower alkyl alcohols and polyhydric alcohols. The lower alkyl alcohols useful herein are monohydric alcohols having from about 1 to about 6 carbons, alternatively ethanol and isopropanol. The polyhydric alcohols useful herein include propylene glycol, hexylene glycol, glycerin, and propane diol.

Alternatively, the aqueous carrier is substantially water. Deionized water is alternatively used. Water from natural sources including mineral cations can also be used, depending on the desired characteristic of the product. Generally, the compositions described herein may comprise from about 20% to about 95%, alternatively from about 30% to about 92%, and alternatively from about 50% to about 90% water.

C. Additional Components

The personal care composition described herein may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, alternatively up to about 5% by weight of the composition.

A wide variety of other additional components can be formulated into the present compositions. These include: other conditioning agents such as hydrolysed collagen with tradename Peptein 2000 available from Hormel, water soluble and water insoluble vitamins such as vitamin A, D, $B_1$, $B_2$, $B_6$, $B_{12}$, C, biotin, vitamin E with tradename Emix-d available from Eisai, panthenol available from Roche, pantothenic acid, panthenyl ethyl ether available from Roche, and their derivatives; hydrolysed keratin, proteins, plant extracts, and nutrients; emollients such as PPG-3 myristyl ether with tradename Varonic APM available from Goldschmidt, Trimethyl pentanol hydroxyethyl ether, PPG-11 stearyl ether with tradename Varonic APS available from Goldschmidt, Stearyl heptanoate with tradename Tegosoft SH available from Goldschmidt, Lactil (mixture of Sodium lactate, Sodium PCA, Glycine, Fructose, Urea, Niacinamide, Glucosamine, Inositol, Sodium Benzoate, and Lactic acid) available from Goldschmidt, Sodium lactate, Sodium PCA, Glycine, Fructose, Urea, Niacinamide, Glucosamine, Inositol, Sodium Benzoate, Lactic acid, Ethyl hexyl palmitate with tradename Saracos available from Nishin Seiyu and with tradename Tegosoft OP available from Goldschmidt; hair-fixative polymers such as amphoteric fixative polymers, cationic fixative polymers, anionic fixative polymers, nonionic fixative polymers, and silicone grafted copolymers; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes, oxidative dyes and interference pigments; hair oxidizing (bleaching) agents, such as hydrogen peroxide, perborate and persulfate salts, carbonate; hair reducing agents such as the thioglycolates; perfumes; and sequestering agents, such as disodium ethylenediamine tetra-acetate; ultraviolet and infrared screening and absorbing agents such as octyl salicylate; antimicrobial agents; suspending agents; viscosity modifiers; nonvolatile solvents or diluents (water soluble and insoluble), pearlescent aids, foam boosters, additional surfactants or nonionic cosurfactants, pediculocides, chelants, skin active agents, sunscreens, UV absorbers, and, water soluble and insoluble amino acids such as asparagine, alanin, indole, glutamic acid, tyrosine, tryptamine, and their salts; and antidandruff agents such as zinc pyrithione, pyridinethione salts, azoles, climbazole, octopirox, salicylic acid, selenium sulfide, particulate sulfur, mixtures thereof.

1. Silicone

The personal care composition described herein may further comprise a silicone compound, in addition to the silicone polymer containing quaternary groups. The silicone compound can be included in an amount of from about 0.1% to about 10%, alternatively from about 0.25% to about 8%, still alternatively from about 0.5% to about 3% by weight of the composition.

The silicone compounds hereof can include volatile soluble or insoluble, or nonvolatile soluble or insoluble silicone conditioning agents. By soluble what is meant is that the silicone compound is miscible with the carrier of the composition so as to form part of the same phase. By insoluble what is meant is that the silicone forms a separate, discontinuous phase from the carrier, such as in the form of an emulsion or a suspension of droplets of the silicone. The silicone compounds herein may be made by conventional polymerization, or emulsion polymerization.

The silicone compounds for use herein will alternatively have a viscosity of from about 1,000 to about 2,000,000 centistokes at 25° C., alternatively from about 10,000 to about 1,800,000 centistokes, and alternatively from about 25,000 to about 1,500,000 centistokes. The viscosity can be measured by means of a glass capillary viscometer as set forth in Dow Corning Corporate Test Method CTM0004, Jul. 20, 1970, which is incorporated by reference herein in its entirety. Silicone compounds of high molecular weight may be made by emulsion polymerization.

Silicone compounds useful herein include polyalkyl polyaryl siloxanes, polyalkyleneoxide-modified siloxanes, silicone resins, amino-substituted siloxanes, and mixtures thereof. The silicone compound is alternatively selected from the group consisting of polyalkyl polyaryl siloxanes, polyalkyleneoxide-modified siloxanes, silicone resins, and mixtures thereof, and alternatively from one or more polyalkyl polyaryl siloxanes.

Polyalkyl polyaryl siloxanes useful here in include those with the following structure (IV)

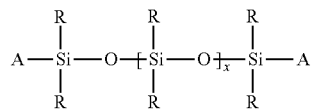

wherein R is alkyl or aryl, and x is an integer from about 7 to about 8,000. A represents groups which block the ends of the silicone chains. The alkyl or aryl groups substituted on the siloxane chain (R) or at the ends of the siloxane chains (A) can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. Suitable A groups include hydroxy, methyl, methoxy, ethoxy, propoxy, and aryloxy. The two R groups on the silicon atom may represent the same group or different groups. Alternatively, the two R groups represent the same group. Suitable R groups include methyl, ethyl, propyl, phenyl, methylphenyl and phenylmethyl. The preferred silicone compounds are polydimethylsiloxane, polydiethylsiloxane, and polymethylphenylsiloxane. Polydimethylsiloxane, which is also known as dimethicone, is especially preferred. The polyalkylsiloxanes that can be used include, for example, polydimethylsiloxanes. These silicone compounds are available, for example, from Momentive Performance Materials in their Element 14® series, and from Dow Corning in their Dow Corning 200 series. Polymethylphenylsiloxanes, for example, from Momentive Performance Materials as SF 1550 methyl phenyl fluid or from Dow Corning as 556 Cosmetic Grade Fluid, are useful herein.

Also preferred, for enhancing the shine characteristics of hair, are highly arylated silicone compounds, such as highly phenylated polyethyl silicone having refractive index of about 1.46 or higher, especially about 1.52 or higher. When these high refractive index silicone compounds are used, they should be mixed with a spreading agent, such as a surfactant or a silicone resin, as described below to decrease the surface tension and enhance the film forming ability of the material.

Another polyalkyl polyaryl siloxane that can be especially useful is a silicone gum. The term "silicone gum," as used herein, means a polyorganosiloxane material having a viscosity at 25° C. of greater than or equal to 1,000,000 centistokes. It is recognized that the silicone gums described herein can also have some overlap with the above-disclosed silicone compounds. This overlap is not intended as a limitation on any of these materials. Silicone gums are described by Petrarch, and others including U.S. Pat. No. 4,152,416, to Spitzer et al., issued May 1, 1979 and Noll, Walter, Chemistry and Technology of Silicones, New York: Academic Press 1968. Also describing silicone gums are Momentive Performance Materials Silicone Rubber Product Data Sheets SE 30, SE 33, SE 54 and SE 76. All of these described references are incorporated herein by reference in their entirety. The "silicone gums" will typically have a mass molecular weight in excess of about 200,000, generally between about 200,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof.

Polyalkyleneoxide-modified siloxanes useful herein include, for example, polypropylene oxide modified and polyethylene oxide modified polydimethylsiloxane. These materials are also known as dimethicone copolyols.

Silicone resins, which are highly crosslinked polymeric siloxane systems, are useful herein. The crosslinking is introduced through the incorporation of tri-functional and tetra-functional silanes with mono-functional or di-functional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units, and hence, a sufficient level of crosslinking, such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Alternatively, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinylchlorosilanes, and tetrachlorosilane, with the methyl substituted silanes being most commonly utilized. Preferred resins are offered by Momentive Performance Materials under trade names_SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art. Without being bound by theory, it is believed that the silicone resins can enhance deposition of other silicone compounds on the hair and can enhance the glossiness of hair with high refractive index volumes.

Other useful silicone resins are silicone resin powders such as the material given the CTFA designation polymethylsilsequioxane, which is commercially available as Tospearl™ from Momentive Performance Materials.

Silicone resins can conveniently be identified according to a shorthand nomenclature system well known to those skilled in the art as the "MDTQ" nomenclature. Under this system, the silicone is described according to the presence of various siloxane monomer units which make up the silicone. Briefly, the symbol M denotes the mono-functional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g., M', D', T', and Q' denote substituents other than methyl, and must be specifically defined for each occurrence. Typical alternate substituents include groups such as vinyl, phenyl, amino, hydroxyl, etc. The molar ratios of the various units, either in terms of subscripts to the symbols indicating the total number of each type of unit in the silicone, or an average thereof, or as specifically indicated ratios in combination with molecular weight, complete the description of the silicone material under the MDTQ system. Higher relative molar amounts of T, Q, T' and/or Q' to D, D', M and/or or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MQ and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

Amino-substituted siloxanes useful herein include those represented by the following structure (V)

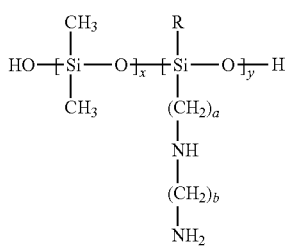

wherein R is $CH_3$ or OH, x and y are integers which depend on the molecular weight, the average molecular weight alternatively being approximately between 5,000 and 10,000; both a and b denote an integer from 2 to 8. This polymer is also known as "amodimethicone".

Suitable amino-substituted siloxane fluids include those represented by the formula (VI)

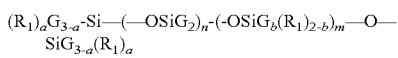

in which G is chosen from the group consisting of hydrogen, phenyl, OH, $C_1$-$C_8$ alkyl and alternatively methyl; a is 0 or an integer having a value from 1 to 3, alternatively 1; b is 0, 1 or 2, alternatively 1; n is a number from 0 to 1,999; m is an integer from 0 to 1,999; the sum of n and m is a number from 1 to 2,000; a and m are not both 0; $R_1$ is a monovalent radical of formula $C_qH_{2q}L$ in which q is an integer from 2 to 8 and L is chosen from the groups —$N(R_2)CH_2$—$CH_2$—$N(R_2)_2$;
—$N(R_2)_2$;
—$N(R_2)^+_3 A^-$; and
—$N(R_2)CH_2$—$CH_2$—$NR_2H^+A^-$ in which $R_2$ is chosen from the group consisting of hydrogen, phenyl, benzyl, a saturated hydrocarbon radical, alternatively an alkyl radical containing from 1 to 20 carbon atoms, and $A^-$ denotes a halide ion.

Highly preferred amino silicones are those corresponding to formula (VI) wherein m=0, a=1, q=3, G=methyl, n is alternatively from about 1500 to about 1700, alternatively about 1600; and L is —$N(CH_3)_2$ or —$NH_2$, alternatively —$NH_2$. Another highly preferred amino silicones are those corresponding to formula (VI) wherein m=0, a=1, q=3, G=methyl, n is alternatively from about 400 to about 600, alternatively about 500; and L is —$N(CH_3)_2$ or —$NH_2$, alternatively —$NH_2$. Such highly preferred amino silicones can be called as terminal aminosilicones, as one or both ends of the silicone chain are terminated by nitrogen containing group.

An especially preferred amino-substituted siloxane corresponding to formula (VI) is the polymer known as "trimethylsilylamodimethicone," of formula (VII):

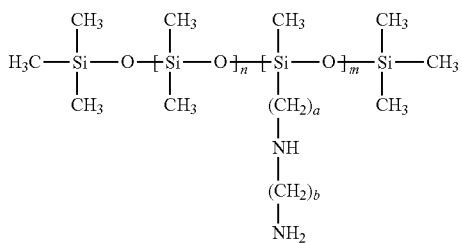

In this formula n and m are selected depending on the molecular weight of the compound desired; both a and b denote an integer from 2 to 8.

In one embodiment of the personal care composition described herein, the silicone compound is contained in the composition in the form of a silicone emulsion. The silicone emulsion herein is a predispersed stable emulsion comprising at least a surfactant, a silicone compound, and water. The surfactant useful herein is any known to the artisan. Silicone emulsions with a high internal phase viscosity are preferred. One preferred example goes by the trade name HMW2220, has an internal phase viscosity of greater than 120,000,000 centistokes, and is available from Dow Corning.

Other modified silicones or silicone copolymers are also useful herein. Examples of these include silicone-based quaternary ammonium compounds (Kennan quats) disclosed in U.S. Pat. Nos. 6,607,717 and 6,482,969; end-terminal quaternary siloxanes disclosed in German Patent No. DE 10036533; silicone aminopolyalkyleneoxide block copolymers disclosed in U.S. Pat. Nos. 5,807,956 and 5,981,681; hydrophilic silicone emulsions disclosed in U.S. Pat. No. 6,207,782; and polymers made up of one or more crosslinked rake or comb silicone copolymer segments disclosed in WO2004/062634.

In alternative embodiments of the personal care composition described herein, the above-noted silicone-based quaternary ammonium compounds may be combined with the silicone polymers described in section A (entitled Silicone Polymer Containing Quaternary Groups) of the instant specification.

2. Polysorbate

The personal care composition described herein may contain a polysorbate, in view of adjusting rheology. Preferred polysorbate useful herein includes, for example, polysorbate-20, polysorbate-21, polysorbate-40, polysorbate-60, and mixtures thereof. Highly preferred is polysorbate-20.

The polysorbate can be contained in the composition at a level by weight of alternatively from about 0.01% to about 5%, alternatively from about 0.05% to about 2%.

3. Polypropylene Glycol

Polypropylene glycol useful herein are those having a weight average molecular weight of from about 200 g/mol to about 100,000 g/mol, alternatively from about 1,000 g/mol to about 60,000 g/mol. Without intending to be limited by theory, it is believed that the polypropylene glycol herein deposits onto, or is absorbed into hair to act as a moisturizer buffer, and/or provides one or more other desirable hair conditioning benefits.

The polypropylene glycol useful herein may be either water-soluble, water-insoluble, or may have a limited solubility in water, depending upon the degree of polymerization and whether other moieties are attached thereto. The desired solubility of the polypropylene glycol in water will depend in large part upon the form (e.g., leave-on, or rinse-off form) of the hair care composition. For example, a rinse-off hair care composition, it is preferred that the polypropylene glycol herein has a solubility in water at about 25° C. of less than about 1 g/100 g water, alternatively a solubility in water of less than about 0.5 g/100 g water, and alternatively a solubility in water of less than about 0.1 g/100 g water.

The polypropylene glycol can be included in the hair conditioning composition described herein at a level of, alternatively from about 0.01% to about 10%, alternatively from about 0.05% to about 6%, still alternatively from about 0.1% to about 3% by weight of the composition.

4. Low Melting Point Oil

Low melting point oils useful herein are those having a melting point of less than about 25° C. The low melting point oil useful herein is selected from the group consisting of: hydrocarbon having from about 10 to about 40 carbon atoms; unsaturated fatty alcohols having from about 10 to about 30 carbon atoms such as oleyl alcohol; unsaturated fatty acids having from about 10 to about 30 carbon atoms; fatty acid derivatives; fatty alcohol derivatives; ester oils such as pentaerythritol ester oils, trimethylol ester oils, citrate ester oils, and glyceryl ester oils; poly α-olefin oils; and mixtures thereof. Preferred low melting point oils herein are selected from the group consisting of: ester oils such as pentaerythritol ester oils, trimethylol ester oils, citrate ester oils, and glyceryl ester oils; poly α-olefin oils; and mixtures thereof, Particularly useful pentaerythritol ester oils and trimethylol ester oils herein include pentaerythritol tetraisostearate, pentaerythritol tetraoleate, trimethylolpropane triisostearate, trimethylolpropane trioleate, and mixtures thereof.

Particularly useful citrate ester oils herein include triisocetyl citrate with tradename CITMOL 316 available from Bernel, triisostearyl citrate with tradename PELEMOL TISC available from Phoenix, and trioctyldodecyl citrate with tradename CITMOL 320 available from Bernel.

Particularly useful glyceryl ester oils herein include triisostearin with tradename SUN ESPOL G-318 available from Taiyo Kagaku, triolein with tradename CITHROL GTO available from Croda Surfactants Ltd., or trilinolein with tradename EFADERMA-F available from Vevy.

Particularly useful poly α-olefin oils herein include polydecenes with tradenames PURESYN 6 having a number average molecular weight of about 500 and PURESYN 100 having a number average molecular weight of about 3000 and PURESYN 300 having a number average molecular weight of about 6000 available from Exxon Mobil Co.

5. Cationic Polymer

Cationic polymers useful herein are those having a weight average molecular weight of at least about 5,000, typically from about 10,000 to about 10 million, alternatively from about 100,000 to about 2 million.

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. Other suitable spacer monomers include vinyl esters, vinyl alcohol (made by hydrolysis of polyvinyl acetate), maleic anhydride, propylene glycol, and ethylene glycol. Other suitable cationic polymers useful herein include, for example, cationic celluloses, cationic starches, and cationic guar gums.

6. Polyethylene Glycol

Polyethylene glycol can also be used as an additional component. The polyethylene glycols useful herein that are especially preferred are PEG-2M wherein n has an average value of about 2,000 (PEG-2M is also known as tradename Polyox WSR® N-10 from Union Carbide and as tradename PEG-2,000); PEG-5M wherein n has an average value of about 5,000 (PEG-5M is also known as tradename Polyox WSR® N-35 and as tradename Polyox WSR® N-80, both from Union Carbide and as tradename PEG-5,000 and tradename Polyethylene Glycol 300,000); PEG-7M wherein n has an average value of about 7,000 (PEG-7M is also known as tradename Polyox WSR® N-750 from Union Carbide); PEG-9M wherein n has an average value of about 9,000 (PEG-9M is also known as tradename Polyox WSR® N-3333 from Union Carbide); and PEG-14M wherein n has an average value of about 14,000 (PEG-14M is also known as tradename Polyox WSR® N-3000 from Union Carbide). As used herein "n" refers to the number of ethylene oxide units in the polymer.

Method of Use

The hair conditioning compositions described herein are used in conventional ways to provide conditioning and other benefits. Such method of use depends upon the type of composition employed but generally involves application of an effective amount of the product to the hair or scalp, which may then be rinsed from the hair or scalp (as in the case of hair rinses) or allowed to remain on the hair or scalp (as in the case of gels, lotions, creams, and sprays). "Effective amount" means an amount sufficient enough to provide a dry conditioning benefit. In general, from about 1 g to about 50 g is applied to the hair or scalp.

The composition may be applied to wet or damp hair prior to drying of the hair. Typically, the composition is used after shampooing the hair. The composition is distributed throughout the hair or scalp, typically by rubbing or massaging the hair or scalp. After such compositions are applied to the hair, the hair is dried and styled in accordance with the preference of the user. In the alternative, the composition is applied to dry hair, and the hair is then combed or styled in accordance with the preference of the user.

Product Forms

The hair conditioning compositions described herein can be in the form of rinse-off products or leave-on products, can be opaque, and can be formulated in a wide variety of product forms, including but not limited to creams, gels, emulsions, mousses and sprays.

The hair conditioning compositions described herein further relates to aqueous emulsions comprising at least one polyorganosiloxane compound and/or at least one polyorganosiloxane composition as defined above. Such aqueous emulsions alternatively comprise at least 30 weight percent, alternatively at least 50 weight percent, still alternatively at least 80 weight percent water based on the total weight of the emulsions.

The hair conditioning compositions described herein may be suitable for rinse-off products and leave-on products, and are particularly useful for making products in the form of a rinse off conditioner.

NON-LIMITING EXAMPLES

The compositions illustrated in the following examples and tables exemplify specific embodiments of the hair conditioning compositions described herein, but are not intended to be limiting thereof. Other modifications can be undertaken by the skilled artisan without departing from the spirit and scope of this invention.

The compositions illustrated in the following examples are prepared by conventional formulation and mixing methods, an example of which is described below. All exemplified amounts are listed as weight percents and exclude minor materials such as diluents, preservatives, color solutions, imagery ingredients, botanicals, and so forth, unless otherwise specified.

Exemplary Silicone Quaternary Polymers A-E below all include the following structure and the substituents listed in Table 1:

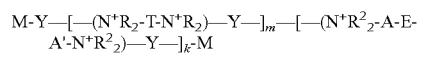

TABLE 1

| Variable | Silicone Quaternary Polymer A | Silicone Quaternary Polymer B | Silicone Quaternary Polymer C | Silicone Quaternary Polymer D | Silicone Quaternary Polymer E |
|---|---|---|---|---|---|
| M | lauric ester | lauric ester | lauric ester | lauric ester | lauric ester |
| Y | K—S—K | K—S—K | K—S—K | K—S—K | K—S—K |
| K | $CH_2$—CHOH—$CH_2$—O—$C_3H_6$ | $CH_2$—CHOH—$CH_2$—O—$C_3H_6$ | $CH_2$—CHOH—$CH_2$—O—$C_3H_6$ | $CH_2$—CHOH—$CH_2$—O—$C_3H_6$ | $CH_2$—CHOH—$CH_2$—O—$C_3H_6$ |
| S | PDMS block with 368 siloxane units | PDMS block with 368 siloxane units | PDMS block with 368 siloxane units | PDMS block with 450 siloxane units | PDMS block with 368 siloxane units |
| R, $R^2$ | methyl | methyl | methyl | methyl | methyl |
| T | $C_6H_{12}$ | $C_6H_{12}$ | $C_6H_{12}$ | $C_6H_{12}$ | $C_6H_{12}$ |
| A | $CH_2$—COO— | $CH_2$—COO— | $CH_2$—COO— | $CH_2$—COO— | $CH_2$—COO— |
| A' | CO—$CH_2$ | CO—$CH_2$ | CO—$CH_2$ | CO—$CH_2$ | CO—$CH_2$ |
| E | Ethylene oxide ($CH_2$—$CH_2$—O) with average degree of ethoxylation of 2 | Ethylene oxide ($CH_2$—$CH_2$—O) with average degree of ethoxylation of 34 | Propylene oxide ($CH_2$—CH($CH_3$)—O) with average degree of propoxylation of 3.5 | Propylene oxide ($CH_2$—CH($CH_3$)—O) with average degree of propoxylation of 3.5 | Ethylene oxide ($CH_2$—$CH_2$—O) with average degree of ethoxylation of 2 |
| Ratio of silicone blocks:alkylene oxide blocks | 1:1 | 9:1 | 9:1 | 9:1 | 7:3 |
| Total Viscosity | 4700 mPa·s | 2800 mPa·s | 2600 mPa·s. | 5400 mPa·s. | 6000 mPa·s. |

Silicone Emulsion

| | A | B | C | D | E |
|---|---|---|---|---|---|
| Water | q.s. | q.s. | q.s. | q.s. | q.s. |
| C11-15 Pareth-5 [1] | 1.0 | 1.4 | 1.0 | | |
| C11-15 Pareth-12 [2] | 1.0 | 2.0 | | | |
| Silicone Quaternary Polymer A | 20.0 | | | | |
| Silicone Quaternary Polymer B | | 10.0 | | | |
| Silicone Quaternary Polymer C | | | 10.0 | | |
| Silicone Quaternary Polymer D | | | | 20.0 | |
| Silicone Quaternary Polymer E | | | | | 20.0 |

| Components | Ex 1 | Ex 2 | Ex 3 | Ex 4 | Ex 5 | Ex 6 | Ex 7 | Ex 8 | Ex 9 |
|---|---|---|---|---|---|---|---|---|---|
| Silicone Emulsion A | 5.0 | | | | | | | | |
| Silicone Emulsion B | | 10.0 | | | | | | | |
| Silicone Emulsion C | | | 5.0 | | | 2.5 | | | |
| Silicone Emulsion D | | | | 10.0 | | | 5.0 | | |
| Silicone Emulsion E | | | | | 7.5 | | | 10.0 | 7.5 |
| Behenyl trimethyl ammonium chloride | 2.25 | 2.25 | 2.25 | 0.5 | 0.5 | 0.5 | 0.5 | 0.5 | 0.5 |
| Isopropyl alcohol | 0.6 | 0.6 | 0.6 | 1.8 | 1.8 | 1.8 | 1.8 | 1.8 | 1.8 |
| Behentrimonium methosulfate | | | | | | | | | |

TABLE 1-continued

| Cetyl alcohol | 1.9 | 1.9 | 1.1 | 1.1 | 1.1 | 1.1 | 1.1 | 1.1 |
|---|---|---|---|---|---|---|---|---|
| Stearyl alcohol | 4.6 | 4.6 | 2.8 | 2.8 | 2.8 | 2.8 | 2.8 | 2.8 |
| Methylchloroisothiazonlinone/ Methylisothiazonlinone | .0005 | .0005 | .0005 | .0005 | .0005 | .0005 | .0005 | .0005 |
| Perfume | 0.55 | 0.55 | 0.5 | 0.5 | 0.5 | 0.7 | 0.7 | 0.7 |

[1] Tergitol 15-S-5, from The Dow Chemical Company
[2] Tergitol 15-S-12, from The Dow Chemical Company It is further noted that terms like "alternatively," "usually", "generally," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the hair conditioning compositions described herein.

For the purposes of describing and defining the hair conditioning compositions described herein it is additionally noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the hair conditioning compositions described herein are identified herein as preferred or particularly advantageous, it is contemplated that the hair conditioning compositions described herein are not necessarily limited to these preferred aspects of the invention.

All documents cited in the Detailed Description of the Invention are, in relevant part, incorporated herein by reference; the citation of any document is not to be construed as an admission that it is prior art with respect to the hair conditioning compositions described herein. To the extent that any meaning or definition of a term in this written document conflicts with any meaning or definition of the term in a document incorporated by reference, the meaning or definition assigned to the term in this written document shall govern.

What is claimed is:

1. A hair conditioning composition comprising:
   a) a silicone polymer comprising:
      i. one or more quaternary groups;
      ii. at least one silicone block comprising greater than 200 siloxane units;
      iii. at least one polyalkylene oxide structural unit; and
      iv. at least one terminal ester group;
      wherein said silicone polymer has a viscosity of 500 mPa·s to 100,000 mPa·s at 20° C. at 100% concentration of said silicone polymer with no additional solvents and a shear rate of 0.1 s$^{-1}$,
      wherein said silicone polymer is added to create a pre-emulsified dispersion with a particle size of less than about 1 micron, and
   b) a gel matrix comprising:
      i. a cationic surfactant;
      ii. a high melting point fatty compound, wherein the high melting point fatty compound has a melting point of about 25° C. or higher; and
      iii. an aqueous carrier;
      wherein said silicone polymer is mixed with said gel matrix.

2. The hair conditioning composition of claim 1, wherein said silicone block comprises from about 300 to about 500 siloxane units.

3. The hair conditioning composition of claim 1, wherein said silicone polymer is present in an amount of from about 0.05% to about 15% by weight of the composition.

4. The hair conditioning composition of claim 1, wherein said silicone polymer is present in an amount of from about 0.1% to about 10% by weight of the composition.

5. The hair conditioning composition of claim 1, wherein said silicone polymer is present in an amount of from about 0.15% to about 5% by weight of the composition.

6. The hair conditioning composition of claim 1, wherein the silicone polymer includes a viscosity from 500 mPa·s to 50,000 mPa·s.

7. The hair conditioning composition of claim 6, wherein the silicone polymer includes a viscosity from 500 mPa·s to 5000 mPa·s.

8. The hair conditioning composition of claim 1, wherein said cationic surfactant is present in an amount of from about 0.1% to about 10% by weight of the composition.

9. A method of providing improved conditioning benefits to hair or skin, said method comprising the step of applying to said hair or skin the hair conditioning composition of claim 1.

* * * * *